US011351021B2

(12) United States Patent
Patel et al.

(10) Patent No.: US 11,351,021 B2
(45) Date of Patent: Jun. 7, 2022

(54) QUILTED IMPLANTABLE GRAFT

(71) Applicant: Cook Biotech Incorporated, West Lafayette, IN (US)

(72) Inventors: Umesh H. Patel, West Lafayette, IN (US); Jeffrey Miller, East Haven, CT (US); Neal E. Fearnot, West Lafayette, IN (US); Mark W. Bleyer, West Lafayette, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 310 days.

(21) Appl. No.: 15/084,080

(22) Filed: Mar. 29, 2016

(65) Prior Publication Data

US 2016/0206785 A1 Jul. 21, 2016

Related U.S. Application Data

(63) Continuation of application No. 12/965,205, filed on Dec. 10, 2010, now Pat. No. 9,295,757, which is a
(Continued)

(51) Int. Cl.
*A61F 2/02* (2006.01)
*A61F 2/00* (2006.01)
(Continued)

(52) U.S. Cl.
CPC .......... *A61F 2/0063* (2013.01); *A61F 2/0077* (2013.01); *A61F 2/02* (2013.01);
(Continued)

(58) Field of Classification Search
CPC ........ A61F 2/0063; A61F 2/0077; A61F 2/02; A61F 2/0045; A61L 27/3633;
(Continued)

(56) References Cited

U.S. PATENT DOCUMENTS 1,592,433 A   1/1921  Belcher
2,756,746 A * 7/1956  Olga ............... A01K 13/007
                                           128/846
(Continued)

FOREIGN PATENT DOCUMENTS

CN    1705559       12/2005
CN    101766843 A    7/2010
(Continued)

OTHER PUBLICATIONS

Heeschen, C., et al. "Nicotine Stimulates Angiogenesis and Promotes Tumor Growth and Atherosclerosis", Nature Medicine, vol. 7, No. 7, Jul. 2001, pp. 833-839.
(Continued)

*Primary Examiner* — Jing Rui Ou
(74) *Attorney, Agent, or Firm* — Woodard Emhardt Henry Reeves & Wagner LLP

(57) ABSTRACT

Described are embodiments of a multilaminate or multiple layer implantable surgical graft with an illustrative graft comprising a remodelable collagenous sheet material, the graft including one or more interweaving members to stitch together the graft to help prevent the layers from delaminating or separating during handling and the initial stages of remodeling. The interweaving members may comprise lines of suture, thread, individual stitches, strips of material, etc. that are woven through the layers of biomaterial in a desired pattern. In one embodiment, the interweaving members comprise a pharmacologically active substance, such as a drug, growth factors, etc. to elicit a desired biological response in the host tissue. In another embodiment, the graft further comprises a reinforcing material, such as a synthetic mesh, within the layers of remodelable biomaterial and stitched together by one or more interweaving members.

24 Claims, 7 Drawing Sheets

Related U.S. Application Data continuation-in-part of application No. 12/482,002, filed on Jun. 10, 2009, now Pat. No. 10,688,219.

(60) Provisional application No. 61/060,316, filed on Jun. 10, 2008.

(51) Int. Cl.
  *A61L 27/50* (2006.01)
  *A61L 31/00* (2006.01)
  *A61L 27/36* (2006.01)

(52) U.S. Cl.
  CPC ....... *A61L 27/3625* (2013.01); *A61L 27/3629* (2013.01); *A61L 27/3633* (2013.01); *A61L 27/50* (2013.01); *A61L 31/005* (2013.01)

(58) Field of Classification Search
  CPC .. A61L 27/3625; A61L 27/3629; A61L 27/50; A61L 31/005
  See application file for complete search history.

(56) References Cited

U.S. PATENT DOCUMENTS

| | | |
|---|---|---|
| 3,562,820 A | 2/1971 | Bernhard |
| 3,998,173 A | 12/1976 | Williamson et al. |
| 4,216,774 A | 8/1980 | Graber |
| 4,902,508 A | 2/1990 | Badylak et al. |
| 4,956,178 A | 9/1990 | Badylak et al. |
| 5,038,693 A | 8/1991 | Kourtides et al. |
| 5,281,422 A | 1/1994 | Badylak et al. |
| 5,380,328 A * | 1/1995 | Morgan ............. A61B 17/8071 606/70 |
| 5,546,876 A | 8/1996 | Schilling et al. |
| 5,554,389 A | 9/1996 | Badylak et al. |
| 5,634,931 A | 6/1997 | Kugel |
| 5,635,201 A * | 6/1997 | Fabo ................... A61F 13/0276 424/443 |
| 5,955,110 A | 9/1999 | Patel et al. |
| 5,997,575 A | 12/1999 | Whitson et al. |
| 6,042,534 A * | 3/2000 | Gellman ............... A61F 2/0045 600/30 |
| 6,099,567 A | 8/2000 | Badylak et al. |
| 6,126,686 A | 10/2000 | Badylak et al. |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,206,931 B1 | 3/2001 | Cook et al. |
| 6,270,530 B1 | 8/2001 | Eldridge et al. |
| 6,431,837 B1 | 8/2002 | Velicki |
| 6,736,823 B2 | 5/2004 | Darois et al. |
| 7,070,558 B2 | 7/2006 | Gellman et al. |
| 7,160,333 B2 | 1/2007 | Plouhar et al. |
| 7,371,919 B1 * | 5/2008 | Busam .................. A61F 13/512 604/367 |
| 2001/0002446 A1 | 5/2001 | Plouhar et al. |
| 2002/0038151 A1 | 3/2002 | Plouhar et al. |
| 2002/0049503 A1 * | 4/2002 | Milbocker ............ A61F 2/0036 623/23.72 |
| 2003/0013989 A1 | 1/2003 | Obermiller et al. |
| 2003/0023316 A1 | 1/2003 | Briown et al. |
| 2003/0028165 A1 | 2/2003 | Curro et al. |
| 2003/0078617 A1 | 4/2003 | Schwartz et al. |
| 2003/0212462 A1 * | 11/2003 | Gryska .................. A61F 2/0063 623/23.72 |
| 2004/0039246 A1 * | 2/2004 | Gellman ............... A61F 2/0036 600/30 |
| 2004/0059431 A1 | 3/2004 | Plouhar et al. |
| 2004/0086685 A1 | 5/2004 | Brillhart, III et al. |
| 2004/0172048 A1 * | 9/2004 | Browning ............. A61F 2/0063 606/151 |
| 2004/0267362 A1 | 12/2004 | Hwang et al. |
| 2005/0021141 A1 | 1/2005 | Bleyer et al. |
| 2005/0027307 A1 | 2/2005 | Schwartz et al. |
| 2005/0165425 A1 | 7/2005 | Croce et al. |
| 2005/0187604 A1 | 8/2005 | Eells et al. |
| 2005/0249771 A1 | 11/2005 | Malaviya et al. |
| 2005/0249772 A1 | 11/2005 | Malaviya et al. |
| 2005/0267325 A1 * | 12/2005 | Bouchier ......... A61B 17/06004 600/37 |
| 2006/0020333 A1 | 1/2006 | Lashinski |
| 2006/0029639 A1 | 2/2006 | Morinaga et al. |
| 2006/0141012 A1 | 6/2006 | Gingras |
| 2006/0178683 A1 | 8/2006 | Shimoji et al. |
| 2007/0260268 A1 | 11/2007 | Bartee et al. |
| 2007/0288040 A1 | 12/2007 | Ferree |
| 2008/0109017 A1 | 5/2008 | Herweck et al. |
| 2009/0318752 A1 | 12/2009 | Evans et al. |
| 2010/0028396 A1 | 2/2010 | Ward et al. |

FOREIGN PATENT DOCUMENTS

| | | | |
|---|---|---|---|
| EP | 1 577 083 A1 | 9/2005 | |
| EP | 1577083 A1 | 9/2005 | |
| WO | WO 1998/22158 | 5/1998 | |
| WO | WO 1998/25637 | 6/1998 | |
| WO | WO 2005/020847 | 3/2005 | |
| WO | WO 2007/019062 * | 9/2007 | ........... A61F 2/0045 |
| WO | WO 2009/152215 A2 | 12/2009 | |

OTHER PUBLICATIONS

Johnson, C. et al. "Matrix Matalloproteinase-9 is Required for Adequate Angiogenic Revascularization of Ischemic Tissues—Potential Role in Capillary Branching", Circulation Research (2004) 94;262-268. American Heart AssociatiOn, Dallas, TX.

Google Patents English Translation of Abstract, CN 101766843A, Entitled, Artificial Bone With Porous Laminated Structure and Passages and Preparation Method Thereof, Published Jun. 19, 2013, Applicant: Tsinghua University. English translation obtained Jul. 1, 2014.

* cited by examiner

QUILTED IMPLANTABLE GRAFT

REFERENCE TO RELATED APPLICATIONS

This application is a continuation of U.S. application Ser. No. 12/965,205, now U.S. Pat. No. 9,295,757, which is a continuation-in-part of U.S. application Ser. No. 12/482,002, filed Jun. 10, 2009, which claims the benefit of U.S. Provisional Application No. 61/060,316, filed Jun. 10, 2008, each of which is hereby incorporated by reference.

BACKGROUND

The present invention relates generally to implantable naturally derived biomaterials used to reinforce and/or regenerate native tissue.

Remodelable tissue grafts harvested as intact sheets from a mammalian source and processed to remove cellular debris advantageously retain the native structure of extracellular collagen matrix (ECM). This matrix of collagen fibers provides a scaffold to facilitate and support tissue ingrowth, particularly in bioactive graft materials, such as porcine small intestinal submucosa or SIS (Surgisis® Biodesign™, Cook Medical, Bloomington Ind.), that is processed to retain an effective level of growth factors and other constituents that stimulate angiogenesis.

While sheet-derived biomaterials advantageously retain the native structure of the collagen matrix, the use of individual sheets is not optimal for certain clinical applications, such as when repairing or reinforcing a body wall defect (e.g., a hernia). Single layer harvested sheets typically lack the requisite strength and durability when hydrated to permit fixation by suturing or other techniques and provide adequate reinforcement as the implanted collagen matrix degrades and is replaced. To address this limitation, overlapping sheets are laminated together by one of several known techniques, such as vacuum pressing, lyophlization (including press lyophilization), chemical cross-linking, etc., forming a more durable multilaminate construct comprising up to eight layers or more.

Multilaminate implantable ECM grafts have been demonstrated to be effective for clinical applications such as hernia repair, eliminating some of the complications associated with permanent polymeric surgical meshes, which are not resorbed by body. One potential issue with these multilaminate constructs is that the bonded layers can sometimes partially delaminate during handling after hydration, which can make the graft more difficult to suture into place. Furthermore, the separating layers of sheet material can provide pockets for the formation of a seroma, which can inhibit the remodeling process.

There remain needs for improved and/or alternative method of forming a multilaminate graft material. The present invention is addressed to those needs.

SUMMARY

The present invention provides, in certain aspects an implantable surgical mesh comprising a plurality of sheets of a remodelable or bioactive collagenous material, such as a collagenous extracellular matrix that is harvested intact from a mammalian source (e.g., porcine small intestinal submucosa, bovine pericardium, porcine or human cadaveric dermis, etc.), wherein the one or more sheets of material are affixed to one another by thread, suture, or one or more strips of material, etc., interwoven through the adjoining sheets, thereby providing a primary or supplemental means of fixation to help prevent delamination of the graft or separation of the layers during handling and/or the initial period of remodeling.

In one aspect of the invention, the plurality of remodelable collagenous sheets is bonded together by a method such as vacuum pressing or lyobonding (bonding using the lyophlization process) prior to the interweaving member(s) being woven therethrough. In one embodiment, the interweaving members include one or more lines of bioresorbable suture material, thread, or another interweaving material that is woven through the graft in a lock stitch configuration or other suitable method. The pattern of stitching may vary according to clinical application and preference, one example including a series of suture lines forming diamond pattern or a single suture line, such as a spiral pattern. The stitching may extend across the entirety of the graft or be limited to the peripheral regions to reinforce the edges. In an alternative embodiment, the layers of the graft may be secured with a series of discrete or unconnected stitches that are distributed across the graft, particularly along the periphery thereof.

Another aspect of the invention provides an interweaving member that comprises a length of bioresorbable suture, thread, yarn, or strips that include a bioactive agent, such as a medicaments (e.g., analgesics, anti-inflammatory agents, antibiotics, etc.) or agents/substances to stimulate or improve tissue remodeling (e.g., growth factors), whereby the agent is eluted from the interweaving member after implantation. The bioactive agent may be loaded into the suture material, applied or bonded to the outer surface, or incorporated into a separate drug-containing member comprises a separate portion of selected ones of the interweaving members.

A further embodiment of the invention provides a multilaminate graft comprising a first portion comprising one or more sheets of remodelable material, a second portion comprising one or more sheets of remodelable material, and a synthetic mesh material disposed therebetween. The first and second portions that form a 'sandwich' with the synthetic portion and are affixed to one another by at least one or more interweaving members and may be further bonded together by the same process used to form a multilaminate configuration (e.g., lyobonding, vacuum pressing, etc.) or by the use of a bonding agent (e.g., adhesive).

In certain embodiments, an inventive surgical graft will comprise a remodelable collagenous material and at least one interweaving member. In one such embodiment, the remodelable collagenous material will comprise a plurality of sheets disposed in a multilayer configuration, and the at least one interweaving member will be interwoven through the plurality of sheets of remodelable collagenous material such that the sheets are affixed together. In this and some other inventive constructs, at least one interweaving member present in the construct might comprise a bioresorbable material. Additionally or alternatively, an interweaving member might comprise a length of suture, thread, or yarn. An interweaving member might comprise a strip of material. An interweaving member might comprise a plurality of discreet suture points, e.g., woven through a plurality of sheets. An interweaving member, in certain aspects, will be interwoven through a plurality of sheets to create a series of stitches. These stitches might be spaced apart by an average distance greater than about 1.5 mm, with a preferred average distance of between 1-7 mm. Such stitches might comprise a plurality of lines forming a pattern across a surgical graft. A pattern might comprise intersecting lines of stitches, for example, such that the pattern comprises a diamond or other shaped configuration on a graft surface. In certain aspects, a pattern might comprise a line of stitches generally coextending with an adjacent line of stitches in at least one of a concentric or a parallel configuration. Additionally or alternatively, a surgical graft might include a first outer surface and a second outer surface facing opposite thereto, and this surgical graft might further comprise first and second regions of the first and second outer surface. In some forms, the stitch density in a first region of a graft will be greater than the stitch density in a second region, and this first region might generally extend along the periphery of a surgical graft. In other forms, the stitch density in a second region of a graft will be greater than the stitch density in a first region, and this second region might generally be disposed about the center of a surgical graft. Additionally or alternatively, a plurality of sheets might comprise a laminated configuration with at least one interweaving member being interwoven therethrough. Optionally, in some forms, a plurality of sheets will not be bonded to adjacent ones except by at least one interweaving member. An interweaving member might include at least one bioactive agent that is impregnated into and/or surface-applied to the interweaving members with the interweaving member being configured to deliver the bioactive agent into adjacent tissue when implanted. A bioactive agent might be selected from a group consisting of an analgesic, an anti-inflammatory agent, and an antibiotic. A bioactive agent might be effective for stimulation of tissue ingrowth into the plurality of sheets of remodelable collagenous material. In certain aspects, a remodelable collagenous material will comprise an extracellular matrix material that has been harvested intact from a mammalian source and subject to processing to render the material acellular while retaining a level of bioactivity therein. An interweaving member might comprise a durable material that is effective to provide reinforcement of a surgical graft during degradation of a remodelable collagenous material and the establishment of new host tissue to replace the remodelable collagenous material. A plurality of sheets might comprise a multilayer laminated configuration that includes a first group of laminated sheets, a second group of laminated sheets, and a synthetic mesh material disposed therebetween, for example, with the first and second group of laminated sheets being affixed to one another by at least one interweaving member. A synthetic mesh material might comprise polymeric strands having a diameter in the range of 0.04 mm to 1.0 mm, preferably in the range of 0.06 mm to 0.5 mm, and even more preferably less than 0.15 mm, with the strands being configured to persist and reinforce tissue about the site of implantation after remodeling of the remodelable extracellular matrix material is substantially complete.

In yet another embodiment, an inventive surgical graft comprises a remodelable extracellular matrix material and at least one interweaving member. The at least one interweaving member is selected from a group consisting of suture, thread and a strip of material. The remodelable extracellular matrix material comprises a plurality of sheets thereof disposed in a multilayer laminated configuration. The sheets are harvested intact from a mammalian source. The at least one interweaving member is interwoven through the plurality of sheets of remodelable extracellular matrix material to form a plurality of stitches further binding the plurality of laminated sheets together. The at least one interweaving member comprises a bioabsorbable material configured to undergo degradation after implantation of the surgical graft. In some forms, the graft will further comprise a bioactive agent that is impregnated into and/or surface-applied to the at least one interweaving member such that the bioactive agent is delivered into adjacent host tissue when implanted therein.

In another aspect, the invention provides a method for manufacturing a surgical graft. This method includes providing a plurality of sheets and at least one interweaving member. The at least interweaving member is selected from a group consisting of suture, thread and a strip of material. The plurality of sheets comprises a remodelable collagenous material that has been harvested from a mammalian source. The sheets are arranged in a multilayer configuration. The method further includes interweaving the at least one interweaving member through the plurality of sheets such that the plurality of sheets are affixed to one another. In some forms, this method will further comprise bonding the plurality of sheets together to form a laminated configuration. Additionally or alternatively, this method might further comprise adding a bioactive agent to the at least one interweaving member such that it is delivered from the at least one interweaving member into tissue disposed adjacent the surgical graft when implanted.

Another embodiment of the present invention provides a multilayer surgical graft that includes a first remodelable extracellular matrix sheet and a second remodelable extracellular matrix sheet with a synthetic mesh material disposed between the two sheets. Additionally, at least one interweaving member is interwoven through the first sheet and the second sheet so as to affix the two sheets together.

Another inventive multilayer surgical graft includes a first remodelable extracellular matrix sheet, a second remodelable extracellular matrix sheet, and a synthetic mesh material with a plurality of mesh openings disposed between the two sheets. The first sheet and the second sheet contact one another through the plurality of mesh openings, e.g., through a first mesh opening, so as to provide a corresponding plurality of contacting regions between the two sheets. In some preferred embodiments, the first sheet and the second sheet are bonded together in these regions to provide a corresponding plurality of bonded regions between the two sheets, and in at least some of these regions, one or more passageways extends through the bonded sheets and through one of the openings in the synthetic mesh material.

In another aspect of the present invention, a multilayer surgical graft includes a first remodelable extracellular matrix sheet, a second remodelable extracellular matrix sheet, and a synthetic mesh material with a plurality of mesh openings disposed between the two sheets. Additionally, a fill material (e.g., an extracellular matrix fill material) resides in each of the mesh openings.

Other objects, embodiments, forms, features, advantages, aspects, and benefits of the present invention shall become apparent from the detailed description and drawings included herein.

DETAILED DESCRIPTION

Figure 1:
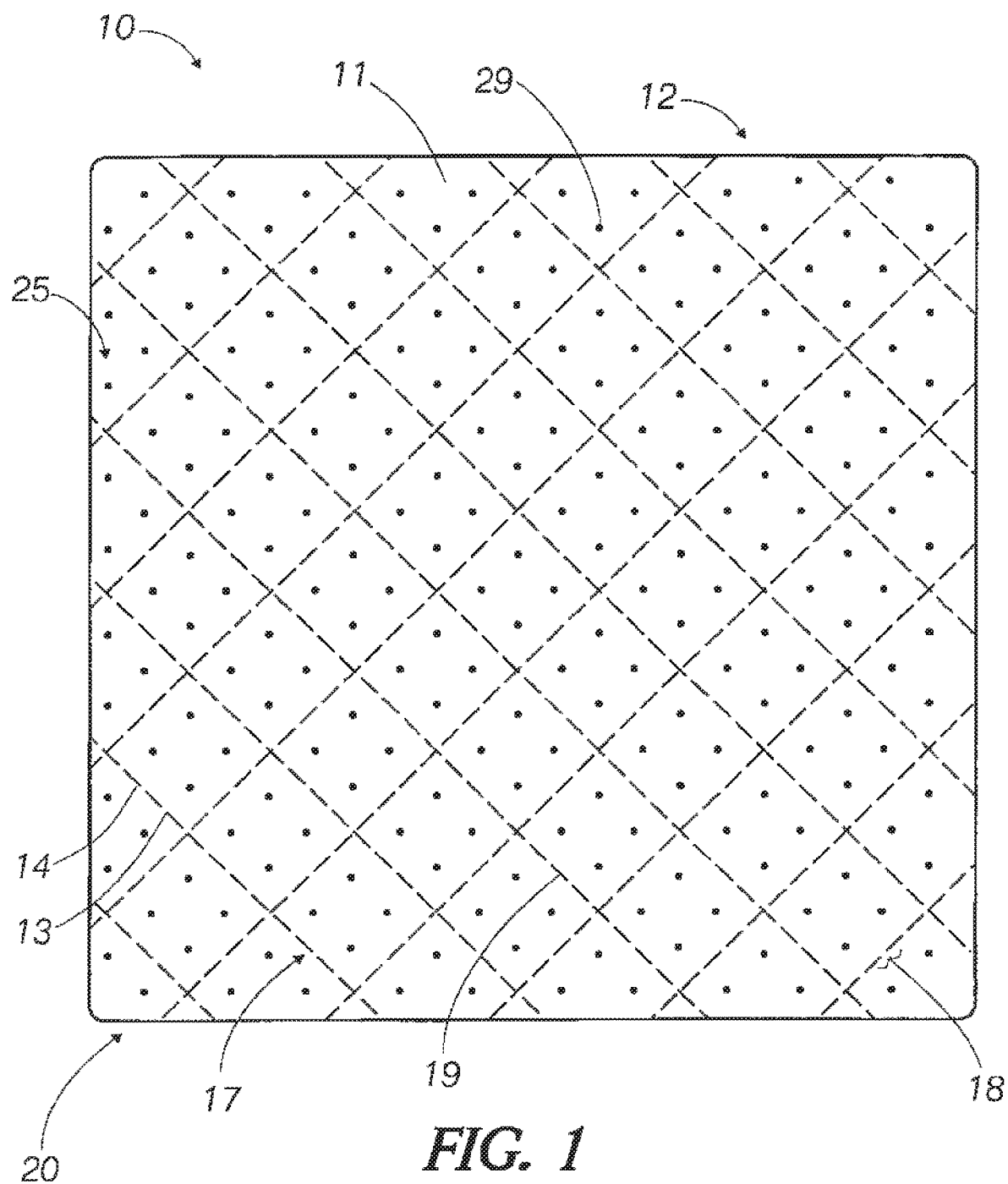
FIG. 1 is a top view of an embodiment of the present invention comprising a multilaminate graft with a first pattern of stitching.

While the present invention may be embodied in many different forms, for the purpose of promoting an understanding of the principles of the present invention, reference will now be made to the embodiments illustrated in the drawings, and specific language will be used to describe the same. It will nevertheless be understood that no limitation of the scope of the invention is thereby intended. Any alterations and further modifications in the described embodiments and any further applications of the principles of the present invention as described herein are contemplated as would normally occur to one skilled in the art to which the invention relates.

As illustrated in the embodiments of FIGS. 1-9, the present invention comprises an implantable surgical graft 10 for repairing or reinforcing tissue, whereby the graft comprises multiple layers 12 of remodelable collagenous sheet material 11 such as sheets derived intact from an animal or human source and processed to retain the ability of the collagen matrix to remodel into site-specific host tissue. While the multiple layers of graft material may be bonded to one another by a process such as lyophilization, vacuum pressing, heat, partial cross-linking, etc., the multilayer graft is further secured together by quilting or stitching the graft using one or more interweaving members 13, such as bioabsorbable suture 14. The pattern 20 of the interweaving members 13 is configured to substantially reduce or prevent delaminating of the graft 10 during handling and/or the early stages of remodeling. Other potential advantages provided by the inclusion of one or more interweaving members will be apparent from the examples discussed later in the text.

Suitable bioremodelable materials can be provided by collagenous extracellular matrix materials (ECMs) possessing biotropic properties. For example, suitable collagenous materials include ECMs such as submucosa, renal capsule membrane, dermal collagen, dura mater, pericardium, serosa, peritoneum or basement membrane layers, including liver basement membrane. Suitable submucosa materials for these purposes include, for instance, intestinal submucosa including small intestinal submucosa, stomach submucosa, urinary bladder submucosa, and uterine submucosa. Such isolated collagenous material can be processed so as to have remodelable, angiogenic properties and promote cellular invasion and ingrowth. Remodelable materials may be used in this context to provide new patient tissue in bodily regions in which inventive constructs are implanted or engrafted.

As prepared and used, the submucosa material and any other ECM used, may optionally retain growth factors or other bioactive components native to the source tissue. For example, the submucosa or other ECM may include one or more growth factors such as basic fibroblast growth factor (FGF-2), transforming growth factor beta (TGF-beta), epidermal growth factor (EGF), and/or platelet derived growth factor (PDGF). As well, submucosa or other ECM used in the invention may include other biological materials such as heparin, heparin sulfate, hyaluronic acid, fibronectin and the like. Thus, generally speaking, the submucosa or other ECM material may include a bioactive component that induces, directly or indirectly, a cellular response such as a change in cell morphology, proliferation, growth, protein or gene expression. A preferred ECM material is porcine small intestinal submucosa (SIS), sold commercially by Cook Medical Inc. (Bloomington, Ind.) under the trade name of Surgisis® Biodesign™ a material that has been shown to remodel effectively into site-specific host tissue in a number of clinical applications.

Further, in addition or as an alternative to the inclusion of such native bioactive components, non-native bioactive components such as those synthetically produced by recombinant technology or other methods, may be incorporated into the submucosa tissue or other ECM material. These non-native bioactive components may be naturally-derived or recombinantly produced proteins that correspond to those natively occurring in the ECM tissue, but perhaps of a different species (e.g. human proteins applied to collagenous ECMs from other animals, such as pigs). The non-native bioactive components may also be drug substances. Illustrative drug substances that may be incorporated into and/or onto the devices include, for example, antibiotics, thrombus-promoting substances such as blood clotting factors, e.g. thrombin, fibrinogen, and the like. These substances may be applied to the graft as a premanufactured step, immediately prior to the procedure (e.g. by soaking the material in a solution containing a suitable antibiotic such as cefazolin), or during or after deployment of the device in the patient.

Submucosa or other ECM tissue used in the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931, or in International Publication No. WO 2008067085 (Jun. 5, 2008) may be characteristic of the submucosa or other ECM tissue used in the present invention.

Submucosa-containing or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with appropriate staining. Such non-collagenous solids can constitute a significant percentage of the dry weight of the ECM material in certain inventive embodiments, for example at least about 1%, at least about 3%, and at least about 5% by weight in various embodiments of the invention.

The submucosa-containing or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels into the materials. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

ECM materials may be essentially free of additional, non-native crosslinking, or may contain additional crosslinking. Such additional crosslinking may be achieved by photo-crosslinking techniques, by chemical crosslinkers, or by protein crosslinking induced by dehydration or other means. However, because certain crosslinking techniques, certain crosslinking agents, and/or certain degrees of crosslinking can destroy the remodelable properties of a remodelable material, where preservation of remodelable properties is desired, any crosslinking of the remodelable ECM material can be performed to an extent or in a fashion that allows the material to retain at least a portion of its remodelable properties.

Now referring to the specific illustrative embodiments, FIG. 1 depicts an embodiment of the present invention comprising a multilaminate graft portion 10 similar to the Surgisis® Biodesign™ Complex Hernia Graft, (a 20×20 cm eight-layer, lyophilized graft construct) and a stitching pattern 20 comprising a series of parallel suture lines 19 (spaced about 2.5 cm apart) extending diagonally across the graft 10 in a first direction, and a second series of parallel suture line extending across the graft in a second direction such that a 'diamond' pattern is created. In the illustrative embodiment, the suture lines 19 are spaced between every other row of apertures 29 that are formed in the graft 10 (typically to allow passage of fluid therethrough) so that each 'diamond' includes a four-perforation cluster therein. In addition to diamond shapes, in certain embodiments, other stitched shapes will be constructed which fully or partially surround one or more perforations occurring in the material. These shapes include circles, ovals, rectangles and various other shapes having curvilinear and/or rectilinear features. The graft 10 may be optionally textured during the lyophilization process, for example, to improve its handling characteristics. Illustratively, a texturing process can include forcibly contacting a hydrated ECM material with another object or material (e.g., a synthetic grate or mesh) while drying the ECM material.

When an inventive construct includes a stitching pattern, this pattern can occupy a variety of shapes and configurations. In some forms, a useful pattern will include one or more stitched lines. Optionally, a pattern that includes a plurality of stitched lines will have lines that intersect one another. In certain embodiments, a pattern that includes a plurality of stitched lines will include a first line that coextends with an adjacent line in a concentric or parallel fashion, or in a combination of the two. As well, when an otherwise perforated material is used in the manufacture of a stitched construct, the stitching and perforations can be arranged in a variety of manners relative to one another. Perforations can include slit and non-slit openings.

In the illustrative interweaving member 13 of FIG. 1, the suture 14 material that stitches together the layers of the graft, may comprise either a synthetic or natural (e.g., collagenous) material. A bioresorbable polymeric suture material, such as 4-0 TRISORB® suture (Samyang Corporation, Seoul, Korea) or other vicryl suture (made from a polyglycolic acid block copolymer), advantageously permits the suture to degrade and be completely resorbed by the body as the graft remodels. However, a non-resorbable synthetic interweaving material, such as a suture made of cross-linked collagen could be used, particularly if there is a desire or need to enhance the strength of the remodelable graft and/or provide continued reinforcement to compliment the remodeled tissue. These types of sutures can be provided in various widths and diameters as will be recognized by those skilled in the art.

As depicted, the suture 14 or other interweaving member 13 is sewn into the graft 10 using a commercial sewing machine adapted for the type of stitching material selected. Applicants have successfully used a model number DDL-9000A-DS sewing machine manufactured by JUKI Corporation (Tokyo, Japan) with TRISORB® suture to create a series of stitches 17 through an eight-layer, lyophilized SIS sheet graft 10. A preferred lateral spacing of parallel suture lines 19 in the illustrative embodiment would be 2-4 cm apart with 3 cm being most preferred. A preferred longitudinal spacing 18 between stitches in a line or row of stitches is at least about 1 mm. In general, the longitudinal spacing between stitches will be in the range of 1-7 mm with a preferred longitudinal spacing of about 3 mm. If more closely spaced, there is a concern that the suture line 19 could weaken the material 11, essentially creating a perforation line that could cause the graft 10 to tear therealong in instances where such tearing is undesirable. If too widely spaced, the suture 14 could unravel along edges when the graft 10 is cut for resizing, increasing the risk of edge delamination. The exemplary interweaving member 13 comprises a series of lock stitches 17, depicted in FIG. 4, in which a first suture 30 is captured from below by a second suture 31 that has penetrated the multiple layers 12 of the graft 10 with the assistance of the sewing needle (not shown) or other suitable device. The lock stitch 17 is simple to create with standard sewing techniques and advantageously resists unraveling; however, other types of stitching including alternatively-arranged lock stitching may be effective to create the quilting pattern. As will be understood by those skilled in the art, with lock stitches, a variety of manipulations can be made to the stitching material(s), the materials being stitched and/or the manner of stitching to vary the final configuration of the stitches. In the illustrative embodiment, the location of the 'lock' between the first suture 30 and second suture 31 can be moved relative to the multiple layers 12, for example, more toward an interior region of the multilayer structure. In some forms, the stitches will be sufficiently taut to form dimples or other indentations in the graft's surface at locations where the lock is pulled into the interior of the graft.

Figure 2:
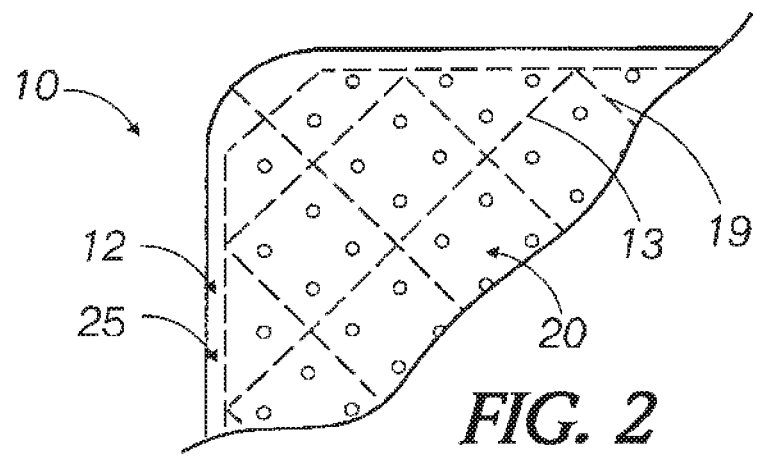
FIG. 2 is a top view of a portion of an embodiment of the present invention comprising a multilaminate graft with the first pattern of stitching and a supplemental line of stitching extending around the periphery of the graft.
Figure 3:
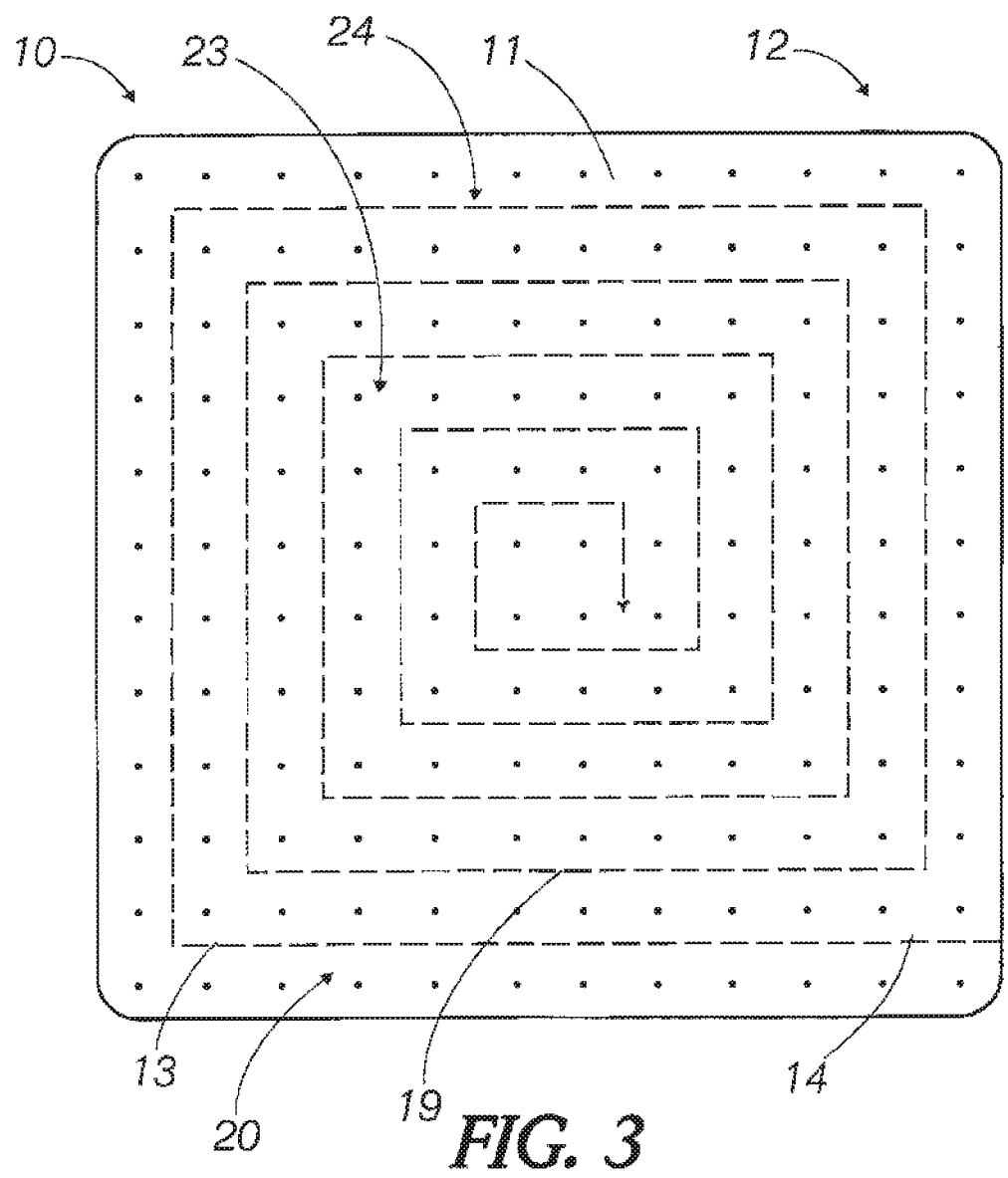
FIG. 3 is a top view of a portion of an embodiment of the present invention comprising a multilaminate graft with a second pattern of stitching.
Figure 4:
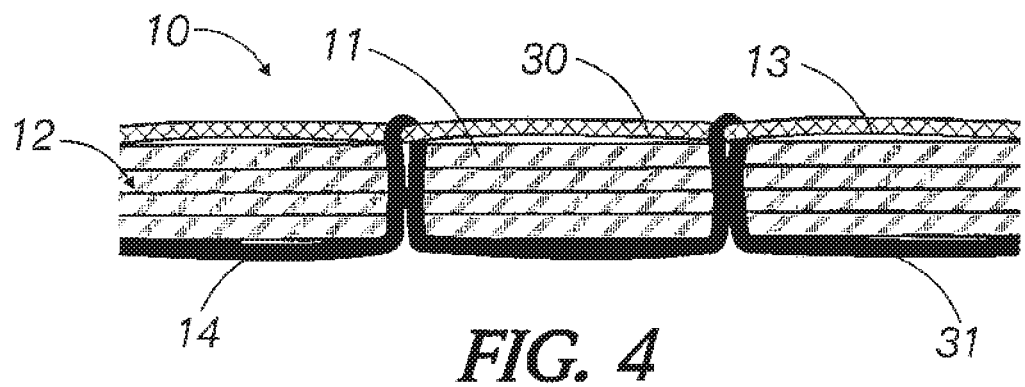
FIG. 4 is a cross-sectional view of the multilaminate graft of the present invention interwoven with a lock stitch.
Figure 5:
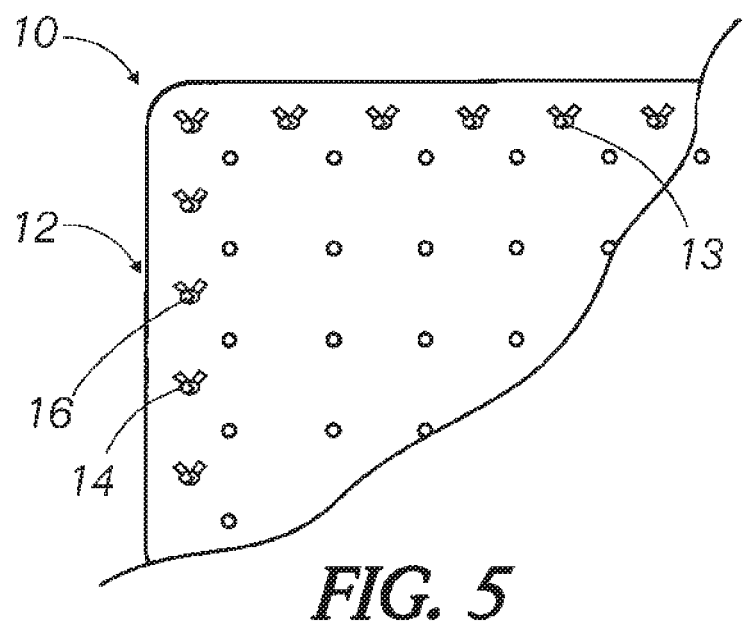
FIG. 5 is a top view of a portion of an embodiment of the present invention comprising a series of discrete stitches distributed about the periphery of the graft.

FIG. 2 depicts an embodiment similar to that of FIG. 1 with the addition of a suture line 19 coextending along the periphery 25 of the graft 10 to further limit the possibility of the multiple layers 12 delaminating therealong during handling and implantation. It is within the spirit of the invention for the quilting pattern 20 to comprise only the peripheral suture line 19 without the additional sutures lines comprising the diamond pattern. Alternatively, as depicted in FIG. 3, the interweaving member 13 may comprise a 'spiral' pattern 20 that extends from the first, inner region 23 of the graft outward to the second, outer region 24 of the graft 10 (or visa versa), resulting in quilting pattern across the entire face of the graft 10 using only a single suture line 19. As an alternative (or supplement) to the one or more suture lines 19, the interweaving member 13 may also comprise a series of discrete fixation points 16, such as the illustrative suture knots of FIG. 5. The knots 16 can be distributed along the periphery 25 of the graft or across the entirety thereof to affix and/or reinforce the multiple layers 12 of the graft 10. The knots can be created individually (as shown) or a chain of knots 16 may be created from a single length of suture with the interconnecting suture 14 being left intact between adjacent knots or clipped away at the knot after the chain is created such that they appear as they would have if created individually. In general, the suture density (or other interweaving member density) can vary across different regions of an inventive construct. Illustratively, there can be a relatively greater amount of suture material occurring in a first region (e.g., periphery) of a graft relative to a second region (e.g., center) of the graft.

Figure 6:
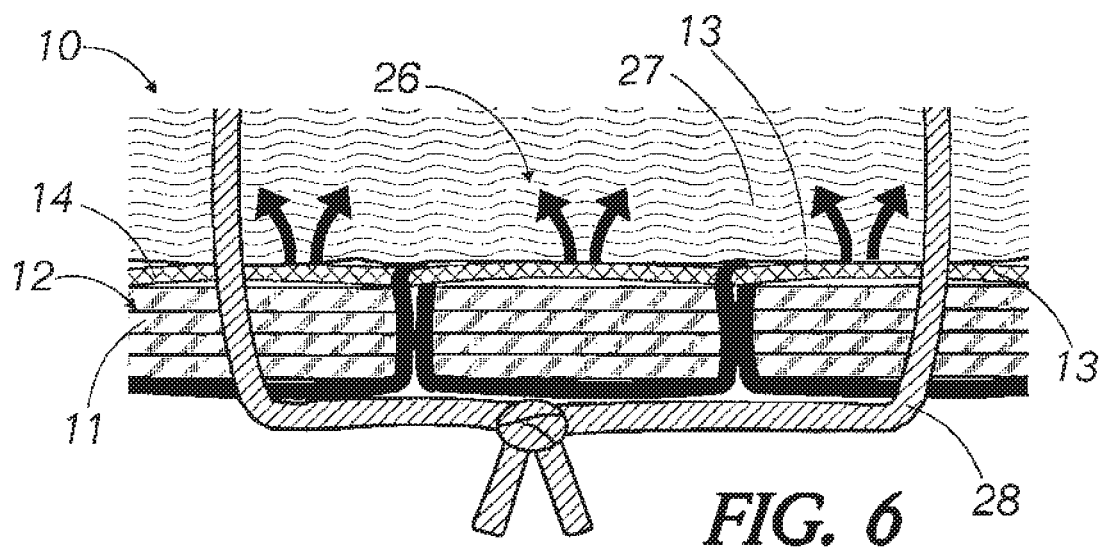
FIG. 6 is a cross-sectional view of an embodiment of the present invention comprising an interweaving member that includes a bioactive agent.

In addition to fulfilling a fixation function, the interweaving member 13 of the present invention may also serve as substrate from which pharmacologically active substance may be delivered. As depicted in FIG. 6, once the graft 10 has been implanted in the patient, such as by attaching it to an area in the body in need of repair using a series of anchoring sutures 28, the pharmacologically active substance 26 is delivered from the interweaving member 13 into the tissue 27 layer that is in contact with the graft. The bioactive agent or drug 26 can be coated onto or applied to the outer surface illustrative suture 14 or other interweaving member, loaded into the polymer or other material during manufacture, or soaked in the agent and taken up through absorption. The dosage and amount of drug or agent applied and delivered is determined by several factors, including the potency thereof, the size/diameter of the suture 14 or interweaving member 13, and the density and distribution pattern of the interweaving member 13 across the graft. Examples of agents appropriate for elution in this matter include compounds selected from a group comprising pharmaceuticals having antimicrobial, analgesic, anti-inflammatory, anti-adhesion, or anti-tumorigeneic properties, and substances that stimulate remodeling, such as growth factors.

Figure 7:
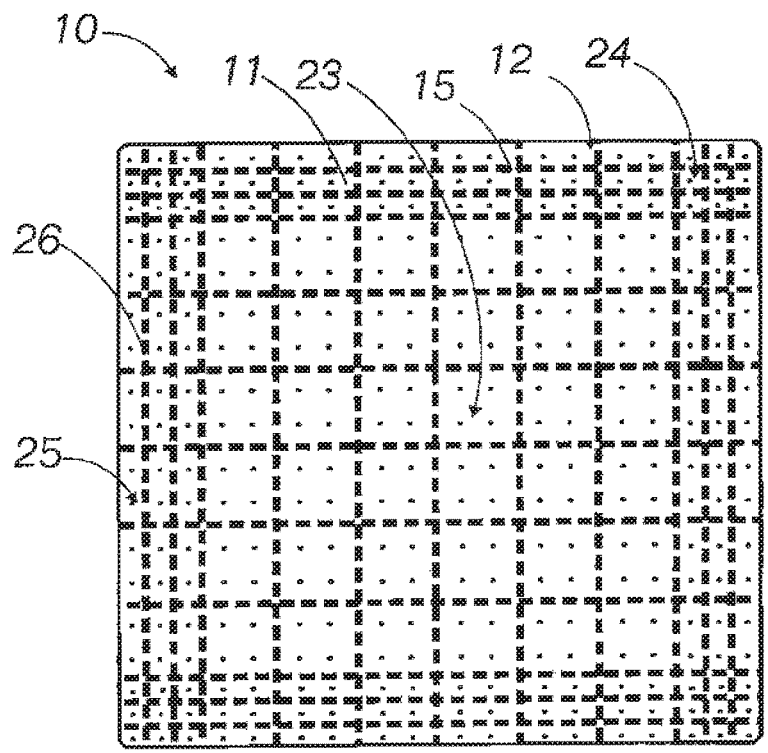
FIG. 7 is a top view of an embodiment of the present invention in which the interweaving members comprise drug-eluting strips of material.

FIG. 7 depicts a graft embodiment of the present invention in which the spacing of the interweaving members 13 is increased along the outer region 24 or periphery 25 of the graft member to increase the available amount of pharmacological agent thereabout. Alternatively, spacing of the interweaving members 13 may be increased in the center portion 23 relative to the outer portion 24, or the agent may be selectively incorporated into the interweaving members 13 within one portion of the graft member 10 while those in another portion do not include the agent. Another strategy for producing increased drug delivery from one portion of the graft 10 relative to another would be to increase the diameter or size of the interweaving members 13 in selective areas so that they can hold more of the active agent than a standard or smaller-sized counterpart.

Figure 8:
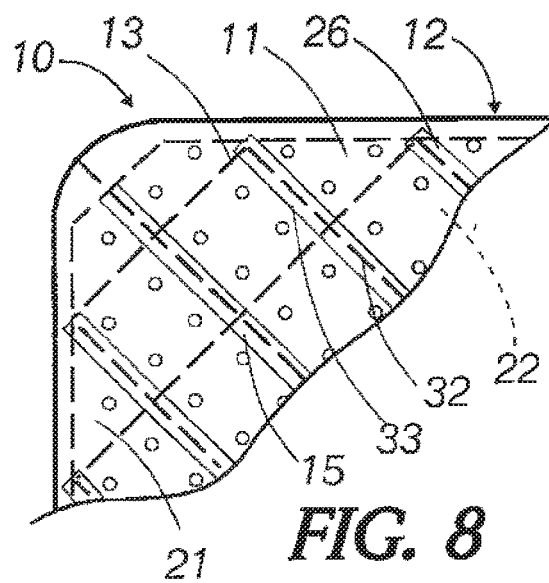
FIG. 8 is a top view of a portion of an embodiment of the present invention comprising drug-eluting members intertwined with selected ones of the interweaving members.

An alternative strategy of delivering a drug or agent 26 into adjacent tissue is depicted by the graft 10 embodiment shown in FIG. 8 in which the interweaving member 13 comprises a first portion 32 that is interwoven through the multiple layers 12 of the graft and second portion 33 comprising the pharmacologically active substance that is affixed to the graft by the first portion of the interweaving member. The second portion 33, which may comprise a strip 15 or other elongate member, may be placed over the outer surface 21 of the graft 10 along selected areas of the intended suture line and sewn into place during the interweaving process (such as with a sewing machine), or the second portion may be interwoven with the first portion 32 after the latter has been woven into the graft, particularly if the first interweaving member includes sufficient spacing with the graft to permit the second member comprising the drug to be inserted therebetween. The drug-containing member may be attached to one or both outer surfaces 21,22 of the graft in identical or varying patterns and may include one type or group of agents on one outer surface 21 of the graft 10 and a different agent or group of agents incorporated thereinto on the opposite side 22 of the graft. The use of a separate strip 15 comprising the agent 26 advantageously allows for the drug-containing portion 33 to be optimized for delivering the agent (i.e., dosage, release rate, location on the graft, etc.), while the first interweaving member portion 32 is optimized for providing the interweaving function (e.g., compatibility with a sewing machine). The second portion 33 or strip 15 may be formed from a porous degradable or bioabsorbable polymer, a biological material, or any biocompatible substrate suitable for carrying and delivering an agent to achieve a predictable and effective biological response. Besides affixing the illustrative strips 15 or members to one or both outer surfaces of the graft, they may be sewn between layers of the biomaterial, particularly if it would be advantageous to control or delay release of the bioactive substance, such as to a later point in the remodeling process.

Figure 9:
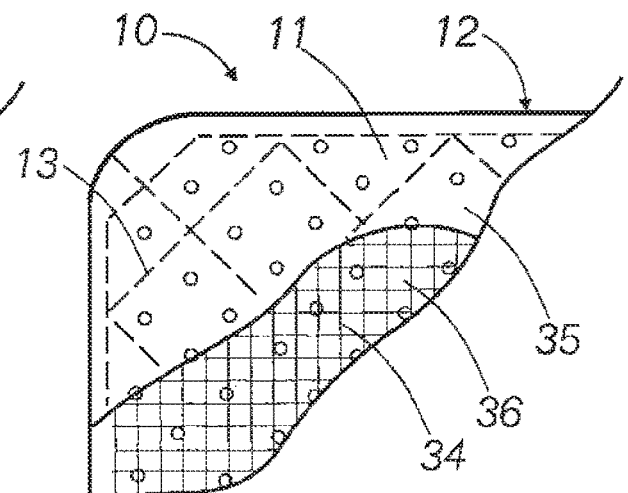
FIG. 9 is a top view of a portion of an embodiment of the present invention comprising a synthetic mesh disposed between layers of the multilaminate graft material.

FIG. 9 depicts a graft 10 embodiment in which the interweaving member 13 affixing the layers 12 of the graft together provides the function of preventing premature delamination thereof when a synthetic mesh 34 is inserted within the layers of biomaterial. In the illustrative embodiment, a medical-grade polypropylene mesh fabric commercially available from ATEX Technologies, Inc. (Pinebluff, N.C.), is sandwiched between a first group of sheets 35 and a second group of sheets 36 (or two individual sheet for a two-layer graft) and the graft is laminated with the synthetic mesh inside. The interweaving members thus provide further fixation to help prevent delamination. Alternatively, the mesh could be inserted between multilayer constructs 35,36 that have been previously lyophilized or otherwise laminated together, such that the stitching from the interweaving member provides the dual function of holding the graft together and preventing delamination. A variety of medical mesh materials including some that are already commercially available can be utilized in the regard as will be recognized by those skilled in the art.

Figure 10A:
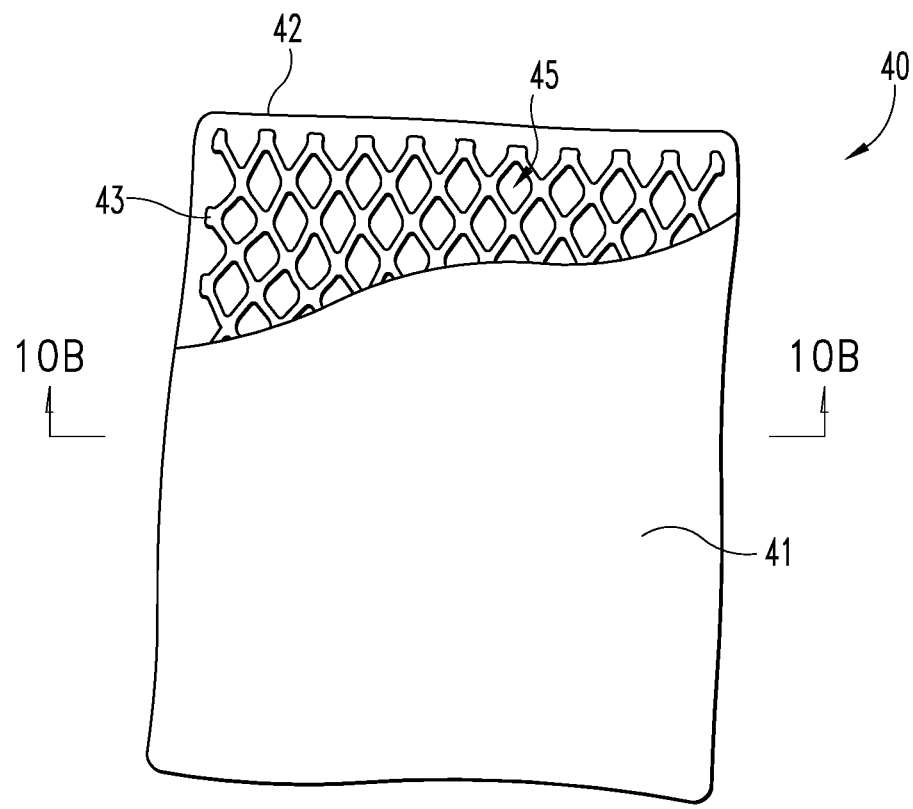
FIG. 10A is a top view of another inventive graft.
Figure 10B:
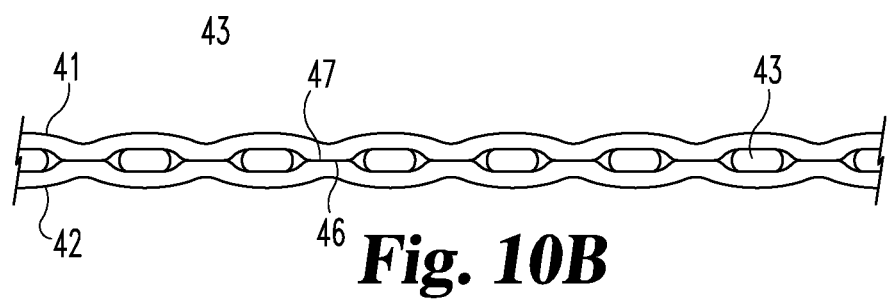
FIG. 10B is a partial, cross-sectional view of the graft of FIG. 10A along the view line 10B-10B shown in FIG. 10A.

FIGS. 10A and 10B depict an illustrative graft construct 40 before it has received an optional interweaving member. Construct 40 includes a first sheet 41 and a second sheet 42 of a remodelable collagenous ECM material. A portion of the first or top sheet 41 has been cut away in FIG. 10A to reveal that a synthetic mesh material 43 (e.g., polypropylene mesh) is disposed between the two sheets. The synthetic mesh includes a plurality of mesh openings 45, and as seen in FIG. 10B, the top and bottom sheets are able to contact one another through the plurality of mesh openings so as to provide a corresponding plurality of contacting regions 46 between the top and bottom sheets. Thus, collagen-containing surfaces from the top sheet and collagen-containing surfaces from the bottom sheet contact one another through the openings 45.

While not necessary to broader aspects of this embodiment, in this illustrative construction, the top and bottom sheets are also bonded to one another in these regions to provide a plurality of bonded regions 47. By bonding the top and bottom sheets in this manner and around the peripheral edges of the mesh material, the synthetic mesh becomes essentially sealed within the surrounding ECM sheets. Either ECM sheet, top or bottom, might be formed with a single ECM layer or a multilayered ECM construct, for example, a sheet incorporating two, three, four, five, six, seven, eight or more individual ECM layers.

Suitable mesh materials include a large variety of mesh or mesh-like structures. Thus, relative to what is shown in FIG. 10A, a suitable mesh can have, among other things, a different number of openings than mesh 43 and/or the shape, size and relative spacing of the openings can be adjusted as desired to suit a particular medical application. Such features can be used to alter the overall percentage of void space in a mesh structure. Illustratively, a mesh opening might be circular, oval, square, rectangular or any other suitable shape.

Additionally, certain mesh or mesh-like structures will be made up of many small filaments, strands or other smaller pieces of material that are interconnected or otherwise associated with one another to form a substantially unitary structure with mesh openings, e.g., like openings 45. When utilized, these smaller pieces may or may not be bonded or directly connected to one another. In alternative forms, a mesh or mesh-like structure may be or include a material that is manufactured (e.g., by extrusion, in a mold or form, etc.) so as to exhibit essentially a unitary structure. Mesh or mesh-like structures can exhibit a flexibility or compliancy or they can be essentially non-flexible or non-compliant, in whole or in part. Mesh structures can be essentially flat in a relaxed condition, or they can exhibit curvature and/or other non-planar features, for example, exhibiting a convexo-concavo or other three-dimensional shape. A mesh or mesh-like structure, in some aspects, will include multiple layers of material. When a mesh structure is multi-layered, the individual layers may or may not be bonded or otherwise connected to one another.

Continuing with FIG. 10B, as occurs in contacting regions 46, when opposing collagen-containing surfaces are in contact with one another certain types of advantageous bonding or fusing can occur between those surfaces. While the extent and types of contact between such surfaces can vary, for example, depending on the overall number, sizing and relative spacing of openings in the mesh material, in certain forms, it will be desirable to fuse or bond the surfaces together to form a more interconnected graft body.

In certain embodiments, contacting collagenous surfaces will desirably be of a character so as to form an attachment to one another by virtue of being dried while compressed against each other. For example, dehydration of these surfaces in forced contact with one another can effectively bond the surfaces to one another, even in the absence of other agents for achieving a bond, although such agents can be used while also taking advantage at least in part on the dehydration-induced bonding. With sufficient compression and dehydration, two collagenous surfaces can be caused to form a generally unitary collagenous structure. Vacuum pressing operations, and the closely bonded nature that they can characteristically impart to the collagen-containing materials, are highly advantageous and preferred in these aspects of the invention. Some particularly useful methods of dehydration bonding ECM materials include lyophilization, e.g. freeze-drying or evaporative cooling conditions.

It is sometimes advantageous to perform drying operations under relatively mild temperature exposure conditions that minimize deleterious effects upon the ECM materials of the invention, for example native collagen structures and potentially bioactive substances present. Thus, drying operations conducted with no or substantially no duration of exposure to temperatures above human body temperature or slightly higher, say, no higher than about 38° C., will preferably be used in some forms of the present invention. These include, for example, vacuum pressing operations at less than about 38° C., forced air drying at less than about 38° C., or either of these processes with no active heating—at about room temperature (about 25° C.) or with cooling. Relatively low temperature conditions also, of course, include lyophilization conditions.

Continuing with FIGS. 10A and 10B, optionally, one or more interweaving members can be incorporated into construct 40 at any point during construction of the graft, for example, before or after laminating any two individual layers together although such products might be used as graft products before receiving an interweaving member, or without ever receiving an interweaving member.

Figure 11A:
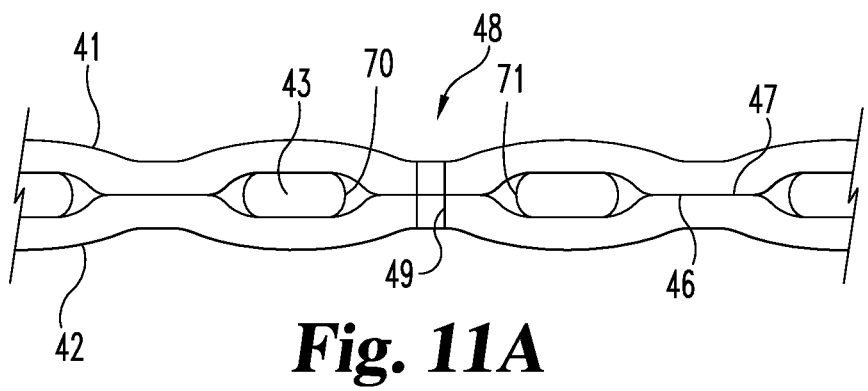
FIG. 11A is a partial, cross-sectional view of another inventive graft.
Figure 11B:
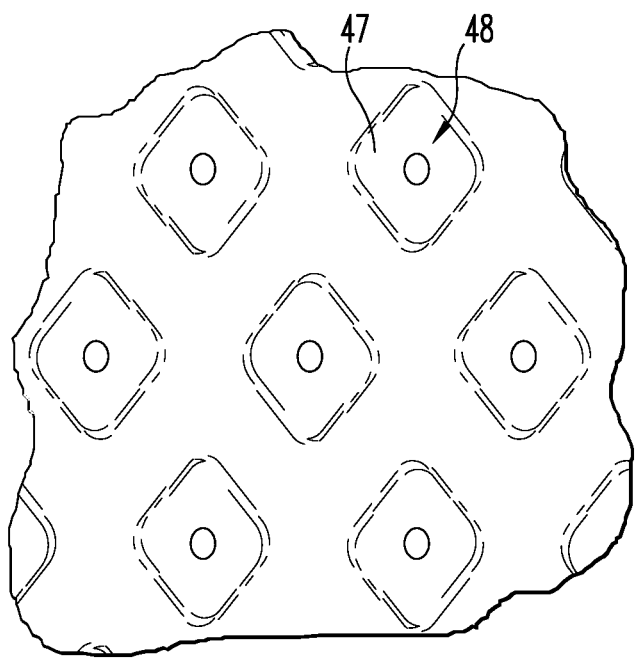
FIG. 11B is a top view of a portion of the graft of FIG. 11A.

FIG. 11A shows a close up view of a graft construct that is similar to that shown in FIG. 10B except that it is additionally incorporates at least one passageway 48 extending through the graft. Passageway 48 includes a passageway wall 49 that traverses the entire thickness of the graft. As can be seen in FIG. 11B, this occurs in an area of the construct where the top and bottom sheets contact one another and are bonded together, that is, generally centered within one of the diamond-shaped mesh openings 45. Each generally cylindrical passageway extends through a corresponding mesh opening 45 although a 1:1 ratio of passageways to synthetic mesh openings is not required. A particular synthetic mesh opening might have two or more passageways associated with it, or it might have none associated with it. While in FIG. 11B the synthetic mesh is hidden from direct view by top sheet 41, the general diamond-shapes of its openings 45 can be discerned since the top and bottom ECM sheets have been vacuum-pressed together through these openings. Yet, it should be understood that the shape of a bonded region need not correspond to the shape of an underlying synthetic mesh opening although this will generally be the case where ECM sheets are pressed around a synthetic mesh and bonded together through openings in the mesh. Whether or not influenced by the shape of an underlying synthetic mesh material, bonded ECM regions can exhibit a variety of shapes including circular, oval, square, rectangular and other suitable shapes.

As shown in FIG. 11B, the area of the bonded region 47 is considerably larger than the diameter of the passageway 48 such that when viewed from the top the bonded region area extends laterally beyond and fully around the passageway. With sufficient bonding between the top and bottom ECM sheets where these sheets meet along the passageway wall 49, the passageway can be substantially isolated from the material of the synthetic mesh. This can allow, for example, bodily fluid and other substances to more easily pass from one side of the graft to the other without being able to directly contact the synthetic material, or at least not for some period of time following implantation. By using various bonding techniques as discussed herein, the ECM sheets can be bonded together to the point of essentially sealing off the passageway from the synthetic mesh. Additionally, the passageway wall 49 can be lined or coated with a variety of substances, e.g., waxes, oils or absorbable polymers such as PLGA to help further separate or block the passageway from the synthetic mesh.

Passageways such as passageway 48 can exhibit a variety of shapes and configurations. When a sheet or layer includes a plurality of passageways, all of the passageways may be of the same type, or alternatively, any one passageway may be shaped and configured differently than any other passageway. A passageway can be or include a slit or a non-slit opening through a sheet or layer. Spacing between or among passageways can vary across a construct. Passageways can be arranged in a pattern of some sort, or an arrangement of passageways can be fully or partially randomized in a construct. The angle at which a passageway extends into and/or trough a material can vary as desired.

Some embodiments will include rows or lines of passageways, although other recognizable groupings of passageways can be employed as well. Passageways may or may not be located across all parts of a graft construct. With some constructs, passageways will occur exclusively or primarily in peripheral regions of the construct, although passageways can additionally or alternatively occur in non-peripheral regions of the construct. As well, a passageway may or may not be pre-existing in a sheet or other component. In instances where a fully or partially manufactured sheet is utilized in the invention, the sheet can be manufactured so as to have one or more passageways in the sheet. In some forms, a sheet or other structure will be provided, and one or more passageways will then be formed in the sheet. Forming a passageway in a construct can occur at any time during formation of the construct and can be accomplished in a variety of ways including some that involve use of scissors, a punch, a knife or scalpel, a laser cutter or any other suitable instrumentation known for creating an opening or passageway in a material.

In certain embodiments, it may be advantageous to process a plurality of slit-type passageways into an inventive construct so as to provide a mesh pattern of the passageways across the construct. In this regard, an inventive construct might include an interior synthetic mesh while also being outfitted with a mesh pattern of passageways across the construct as a whole. Such a mesh pattern of passageways can be useful to provide or add further deformability to a graft structure, and in some case, expandability. In this regard, in some constructs having slit-type passageways, expansion or other deformation of the structure will widen the openings created by the slits of the mesh pattern, by lateral and/or vertical displacement of the edges of the slits relative to one another.

A meshed pattern of passageways or other openings can be created using suitable meshing devices designed for processing skin autograft sections. Such devices can include a cylindrical drum cutter with a plurality of edges for providing the slit pattern of the mesh. A variety of such devices are known and can be used in the invention. For additional information as to meshers, reference may be made to U.S. Pat. Nos. 5,004,468, 6,063,094, 3,472,228, 3,358,688, and 3,640,279. These and other devices incorporating a meshing drum provide for a convenient, high-throughput method of preparing meshed material layers or constructs used in the invention. When used, such devices can be set up to specifically avoid cutting into an underlying synthetic mesh material. Alternatively, one or more layers can be meshed before they are combined with a synthetic mesh material. It will be understood, however, that a mesh pattern can be made by hand-cutting a material or by using appropriate cutting tools with multiple blades to cut the slits to provide the mesh pattern.

Figure 12:
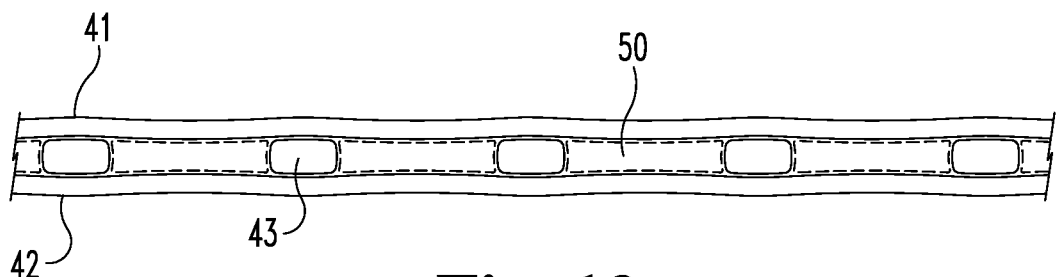
FIG. 12 is a partial, cross-sectional view of yet another inventive graft.

With reference now to FIG. 12, shown is yet another graft construct that is similar to that shown in FIG. 10B except that it additionally includes amounts of a fill material 50 positioned between the top and bottom sheets and generally within each of the mesh openings 45. FIG. 12 shows discrete pockets of fill material where each individual pocket is surrounded by ECM sheets from above and below and by the synthetic mesh material to the sides, although it is certainly possible for these pockets to be interconnected to some degree such as where fill material extends between the pockets along the top and/or bottom surfaces of the mesh material. In some instances, amounts of fill material will wholly separate top and/or bottom surfaces of the synthetic mesh material from the surrounding ECM layers. Additionally, such constructs might be outfitted with one or more passageways like the passageway 48 shown in FIG. 11A so that the passageway would, for example, extend through the top sheet, through fill material residing within the mesh opening, and then through the bottom sheet. In this way, a sort of hybrid passageway wall 49 can be formed, e.g., with parts of the wall being formed by the ECM materials and the intervening fill material.

With regard to fill materials, one or more materials or substances can be introduced into any void space and/or along any surface within an inventive construct. Suitable fill substances include various space filling materials such as remodelable or resorbable materials, for example, a comminuted, fluidized, and/or gelatinous remodelable material as described elsewhere herein, or other substances (e.g., in the form of fluids, pastes, gels, sponges, powders, tissue fragments, segments, strips, layers, etc.), therapeutic agents, e.g. suitable drugs such as antibiotics, antimicrobial agents or the like. Other options include but are not limited to polymer, contrast medium, a non-bioabsorbable material, collagen rods or particulates, a collagenous or gelatinous foam, chitosan, gelatin, oxidized regenerated cellulose, thrombin-fibrin enhanced materials, fibrin glues or other bonding agents, or any suitable combination thereof. As well, the exterior and/or interior of an inventive implantable construct can be coated with and/or the material of the construct can incorporate one or more of these materials or substances or another drug coating, either as-manufactured or by an attending health care provider at the point of surgery.

In one embodiment, a fill material will comprise a comminuted, fluidized, and/or gelatinous remodelable material. For example, a remodelable gel can be formed from fluidized compositions, as illustrated in U.S. Pat. Nos. 5,275,826, 5,516,533, 6,206,931, and/or International Publication No. WO2005020847 (Cook Biotech Incorporated) published Mar. 10, 2005, which are each hereby incorporated by reference in their entirety. In this regard, solutions or suspensions of ECM can be prepared by comminuting and/or digesting ECM with a protease (e.g. trypsin or pepsin), for a period of time sufficient to solubilize the ECM and form substantially a homogenous solution. The ECM starting material is desirably comminuted by tearing, cutting, grinding, shearing or the like. Grinding the ECM in a frozen or freeze-dried state is advantageous, although good results can be obtained as well by subjecting a suspension of pieces of the submucosa to treatment in a high speed blender and dewatering, if necessary, by centrifuging and decanting excess waste. The comminuted ECM can be dried, for example freeze dried, to form a powder. Thereafter, if desired, the powder can be hydrated, that is, combined with water or buffered saline and optionally other pharmaceutically acceptable excipients, to form a fluid composition, e.g. having a viscosity of about 2 to about 300,000 cps at 25° C. The higher viscosity compositions can have a gel or paste consistency. This gelatinous composition can be used as fill material in and/or around a construct of the invention.

Additionally, such gelatinous or flowable materials can include solubilized and/or particulate ECM components, and in preferred forms include ECM gels having suspended therein ECM particles, for example having an average particle size of about 50 microns to about 500 microns, more preferably about 100 microns to about 400 microns. The ECM particulate can be added in any suitable amount relative to the solubilized ECM components, with preferred ECM particulate to ECM solubilized component weight ratios (based on dry solids) being about 0.1:1 to about 200:1, more preferably in the range of 1:1 to about 100:1. The inclusion of such ECM particulates in the ultimate gel can serve to provide additional material that can function to provide bioactivity to the gel (e.g. itself including FGF-2 and/or other growth factors or bioactive substances as discussed herein) and/or serve as scaffolding material for tissue ingrowth.

Figure 13:
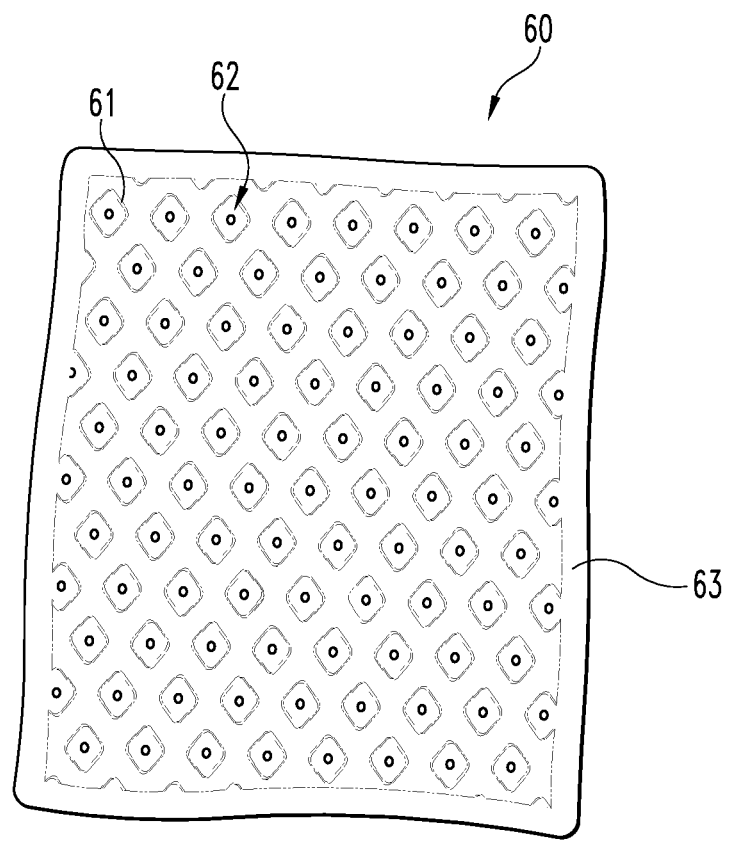
FIG. 13 is a top view of another inventive graft.

FIG. 13 shows an illustrative construct 60 that includes a synthetic mesh material totally encapsulated between and within sheets of a remodelable ECM material. While the actual material of the encapsulated synthetic mesh is hidden from view in this illustration, it is possible to discern its generally diamond-shaped openings through which opposing ECM layers have been bonded together to form bonded regions 61. A single passageway 62 extends through each bonded region. Because the synthetic mesh is slightly smaller in area than the ECM sheets, the full bonding together of the top and bottom ECM layers produces a somewhat wide band or swath 63 of bonded material around the entire periphery of the synthetic mesh. This band, which can exhibit a variety of shapes and sizes according to broader aspects of this embodiment, is a multilayered bonded ECM region void of synthetic mesh material.

The constructs described herein have broad application. In some aspects, inventive products will find use as precursor materials for the later formation of a variety of other medical products, or components thereof. Medical grafts and materials that are already commercially available can be modified in accordance with the present invention as well. In certain embodiments, inventive products are useful in procedures to replace, augment, support, repair, and/or otherwise suitably treat diseased or otherwise damaged or defective patient tissue. Some of the illustrative constructs described herein will be useful, for example, in treating herniated tissue although inventive constructs and materials can be developed and used in many other medical contexts. In this regard, when used as a medical graft, inventive constructs can be utilized in any procedure where the application of the graft to a bodily structure provides benefit to the patient. Illustratively, graft materials of the invention can be processed into various shapes and configurations, for example, into a variety of differently shaped urethral slings, surgical bolster or reinforcement materials (e.g., for use in tissue resection and similar procedures), wound products and other grafts and graft-like materials.

All publications and patent applications cited in this specification are herein incorporated by reference as if each individual publication or patent application were specifically and individually indicated to be incorporated by reference. Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

What is claimed is:

1. A multilayer surgical graft, comprising:
   a first remodelable extracellular matrix sheet having a first multilayer configuration, the first multilayer configuration constituted of two layers of lyophilized extracellular matrix material;
   a second remodelable extracellular matrix sheet having a second multilayer configuration, the second multilayer configuration constituted of two layers of lyophilized extracellular matrix material;
   a reinforcing structure disposed between said first remodelable extracellular matrix sheet and said second remodelable extracellular matrix sheet, the reinforcing structure comprising polymeric strands having a diameter in the range of 0.06 mm to 0.5 mm, the polymeric strands being associated with one another to form a mesh structure, and wherein the polymeric strands persist after implantation and reinforce tissue about the site of implantation of the surgical graft after remodeling of the first and second remodelable extracellular matrix sheets;
   at least one interweaving member interwoven through said first remodelable extracellular matrix sheet and said second remodelable extracellular matrix sheet such that said first remodelable extracellular matrix sheet and said second remodelable extracellular matrix sheet are affixed together;
   wherein the at least one interweaving member includes a first plurality of stitch lines extending diagonally with respect to a first edge opposing a second edge of the surgical graft, and a second plurality of stitch lines extending perpendicular to and intersecting the first plurality of stitch lines so as to form a diamond pattern on the surgical graft;
   wherein stitch lines of the first plurality of stitch lines are parallel to one another and laterally spaced from one another by 2 to 4 cm, and stitch lines of the second plurality of stitch lines are parallel to one another and laterally spaced from one another by 2 to 4 cm; and said reinforcing structure having an outer periphery defined by outermost edges of said mesh structure, and a band of lyophilized extracellular matrix material around the entire outer periphery of the reinforcing structure, said band being void of synthetic mesh material.

2. The multilayer surgical graft of claim 1, wherein:

the polymeric strands include a first plurality of strands extending parallel to the first and second opposite edges of the surgical graft and a second plurality of strands intersecting and extending perpendicular to the first plurality of strands.

3. The multilayer surgical graft of claim 1, comprising bonded regions, wherein said first remodelable extracellular matrix sheet and said second remodelable extracellular matrix sheet are dehydrothermally bonded to one another in said bonded regions.

4. The multilayer surgical graft of claim 1 including passageways extending through said first remodelable extracellular matrix sheet and through said second remodelable extracellular matrix sheet.

5. The multilayer surgical graft of claim 4, wherein said passageways are generally centered within said mesh openings.

6. The multilayer surgical graft of claim 4, wherein said passageways include a generally cylindrical passageway wall.

7. The multilayer surgical graft of claim 4, further comprising a coating material coating a wall of said passageways.

8. The multilayer surgical graft of claim 4, further comprising a resorbable lining material that lines a wall of said passageways.

9. The multilayer surgical graft of claim 1, comprising an open passageway for allowing passage of fluids through the open passageway from a first side of the multilayer surgical graft to a second side of the multilayer surgical graft.

10. The multilayer surgical graft of claim 1, wherein said first remodelable extracellular matrix sheet and said second remodelable extracellular matrix sheet are bonded to one another by a bonding agent.

11. The multilayer surgical graft of claim 10, wherein the bonding agent is an adhesive.

12. The multilayer surgical graft of claim 1, comprising a first bonded region, wherein said first remodelable extracellular matrix sheet and said second remodelable extracellular matrix sheet are heat bonded to one another in said first bonded region.

13. The multilayer surgical graft of claim 12, wherein at least one of said first remodelable extracellular matrix sheet and said second remodelable extracellular matrix sheet include a sheet harvested intact from a mammalian source.

14. The multilayer surgical graft of claim 13, wherein said sheet harvested intact from a mammalian source includes porcine small intestinal submucosa.

15. The multilayer surgical graft of claim 14, wherein said sheet harvested intact from a mammalian source includes bovine pericardium.

16. The multilayer surgical graft of claim 14, wherein said sheet harvested intact from a mammalian source includes porcine or human cadaveric dermis.

17. The multilayer surgical graft of claim 1, wherein said mesh structure is smaller in area than said first remodelable extracellular matrix sheet and said second remodelable extracellular matrix sheet.

18. The multilayer surgical graft of claim 1, wherein said first remodelable extracellular matrix sheet and said second remodelable extracellular matrix sheet are contacting and bonded to one another across only a portion of individual openings over which the first and second remodelable extracellular matrix sheets extend.

19. A multilayer surgical graft, comprising:

a first remodelable extracellular matrix sheet having a first multilayer configuration, the first multilayer configuration constituted of two layers of lyophilized extracellular matrix material;

a second remodelable extracellular matrix sheet having a second multilayer configuration, the second multilayer configuration constituted of two layers of lyophilized extracellular matrix material;

a reinforcing structure disposed between said first remodelable extracellular matrix sheet and said second remodelable extracellular matrix sheet, the reinforcing structure comprising polymeric strands having a diameter in the range of 0.06 mm to 0.5 mm, the polymeric strands being associated with one another to form a mesh structure, and wherein the polymeric strands persist after implantation and reinforce tissue about the site of implantation of the surgical graft after remodeling of the first and second remodelable extracellular matrix sheets; and at least one interweaving member interwoven through said first remodelable extracellular matrix sheet and said second remodelable extracellular matrix sheet; wherein said first and second remodelable extracellular matrix sheets each have a length and a width greater than that of said mesh structure so as to extend across said length and width of said mesh structure and beyond the periphery of the mesh structure;

wherein the surgical graft comprises a first edge opposing a second edge, wherein the at least one interweaving member includes a first plurality of stitch lines extending diagonally with respect to the first and second opposed edges of the surgical graft, and a second plurality of stitch lines extending perpendicular to and intersecting the first plurality of stitch lines so as to form a diamond pattern on the surgical graft;

wherein stitch lines of the first plurality of stitch lines are parallel to one another and laterally spaced from one another by 2 to 4 cm, and stitch lines of the second plurality of stitch lines are parallel to one another and laterally spaced from one another by 2 to 4 cm; and said reinforcing structure having an outer periphery defined by outermost edges of said mesh structure, and a band of lyophilized extracellular matrix material around the entire outer periphery of the reinforcing structure, said band being void of synthetic mesh material.

20. The multilayer surgical graft of claim 19, further including at least one passageway extending through said first remodelable extracellular matrix sheet and said second remodelable extracellular matrix sheet.

21. The multilayer surgical graft of claim 19, wherein the first and second remodelable extracellular matrix sheets are bonded together around the periphery of the mesh structure.

22. A multilayer surgical graft, comprising:

a first remodelable extracellular matrix sheet having a first multilayer configuration, the first multilayer configuration constituted of two layers of lyophilized extracellular matrix material;

a second remodelable extracellular matrix sheet having a second multilayer configuration, the second multilayer configuration constituted of two layers of lyophilized extracellular matrix material;

a reinforcing structure disposed between said first remodelable extracellular matrix sheet and said second remodelable extracellular matrix sheet, the reinforcing structure comprising polymeric strands having a diameter in the range of 0.06 mm to 0.5 mm, the polymeric strands being associated with one another to form a mesh structure, and wherein the polymeric strands persist after implantation and reinforce tissue about the site of implantation of the surgical graft after remodeling of the first and second remodelable extracellular matrix sheets;

said first remodelable extracellular matrix sheet and said second remodelable extracellular matrix sheet contacting and bonded to one another through a plurality of mesh openings in the mesh to provide bonded regions between said first remodelable extracellular matrix sheet and said second remodelable extracellular matrix sheet;

at least one interweaving member interwoven through said first remodelable extracellular matrix sheet and said second remodelable extracellular matrix sheet;

wherein the surgical graft comprises a first edge opposing a second edge, and wherein the at least one interweaving member includes a first plurality of stitch lines extending diagonally with respect to the first and second opposed edges of the surgical graft, and a second plurality of stitch lines extending perpendicular to and intersecting the first plurality of stitch lines so as to form a diamond pattern on the surgical graft;

wherein stitch lines of the first plurality of stitch lines are parallel to one another and laterally spaced from one another by 2 to 4 cm, and stitch lines of the second plurality of stitch lines are parallel to one another and laterally spaced from one another by 2 to 4 cm; and said reinforcing structure having an outer periphery defined by outermost edges of said mesh structure, and a band of lyophilized extracellular matrix material around the entire outer periphery of the reinforcing structure, said band being void of synthetic mesh material.

23. The multilayer surgical graft of claim 22 also comprising a plurality of openings that traverses the entire thickness of the multilayer surgical graft.

24. The multilayer surgical graft of claim 23, wherein the openings comprise slits.

\* \* \* \* \*